US012559447B2

(12) United States Patent
Goris et al.

(10) Patent No.: US 12,559,447 B2
(45) Date of Patent: Feb. 24, 2026

(54) METHODS FOR INCREASING HYDROFORMYLATION CATALYST PREFORMING RATES

(71) Applicant: ExxonMobil Chemical Patents Inc., Baytown, TX (US)

(72) Inventors: Hans Goris, Zaventem (BE); Dries Timmermans, Sint-Katharina-Lombeek (BE); Stephen Beadle, Prairieville, LA (US); Thomas Wesselmann, Baton Rouge, LA (US); Alex Carpenter, Seabrook, TX (US); Travis Reine, Seabrook, TX (US); Edwin Kooke, Machelen (BE); Byron Sevin, St. Francisville, LA (US); Zsigmond Varga, Schaerbeek (BE); Bradley Kontra, Huffman, TX (US)

(73) Assignee: ExxonMobil Chemical Patents Inc., Spring, TX (US)

( * ) Notice: Subject to any disclaimer, the term of this patent is extended or adjusted under 35 U.S.C. 154(b) by 884 days.

(21) Appl. No.: 17/813,213

(22) PCT Filed: Dec. 16, 2020

(86) PCT No.: PCT/EP2020/086386
§ 371 (c)(1),
(2) Date: Jul. 18, 2022

(87) PCT Pub. No.: WO2021/148202
PCT Pub. Date: Jul. 29, 2021

(65) Prior Publication Data
US 2023/0202954 A1     Jun. 29, 2023

Related U.S. Application Data

(60) Provisional application No. 62/965,464, filed on Jan. 24, 2020.

(51) Int. Cl.
*C07C 45/50* (2006.01)
*B01J 31/20* (2006.01)

(52) U.S. Cl.
CPC ............. *C07C 45/505* (2013.01); *B01J 31/20* (2013.01); *B01J 2231/321* (2013.01); *B01J 2531/845* (2013.01)

(58) Field of Classification Search
CPC ... C07C 45/505; B01J 31/20; B01J 2231/321; B01J 2531/845
See application file for complete search history.

(56) References Cited

U.S. PATENT DOCUMENTS

| | | | |
|---|---|---|---|
| 2,802,846 A | 8/1957 | Kern | |
| 3,234,146 A | 2/1966 | Bowe et al. | |
| 4,225,458 A | 9/1980 | Huang et al. | |
| 7,910,782 B2 * | 3/2011 | Van Driessche | ........ C07C 45/50 560/127 |

FOREIGN PATENT DOCUMENTS

| | | |
|---|---|---|
| WO | 2008/122526 A1 | 10/2008 |
| WO | 2021/148202 A1 | 7/2021 |

OTHER PUBLICATIONS

International Preliminary Report on Patentability received for PCT Application No. PCT/EP2020/086386, mailed on Aug. 4, 2022, 8 Pages.
International Search Report and Written Opinion received for PCT Application No. PCT/EP2020/086386, mailed on May 4, 2021, 13 Pages.

* cited by examiner

*Primary Examiner* — Sikarl A Witherspoon

(57) ABSTRACT

Catalyst preforming rates during hydroformylation may decrease in the presence of carbonates. Carbonate mitigation methods may comprise treating a hydroformylation reaction product with an aqueous carboxylic acid under oxidizing conditions to form a deactivated catalyst aqueous solution having a pH of about 4 or less, reducing the hydroformylation reaction product to form a reduced reaction product, conveying a gas stream through the reduced reaction product to strip carbon dioxide therefrom, contacting caustic aqueous solution with the stripped reduced reaction product to form partially spent caustic aqueous solution, combining at least a portion of the partially spent caustic aqueous solution with the deactivated catalyst aqueous solution to form a combined aqueous mixture sufficiently acidic to decompose carbonate, and extracting a Group 9 transition metal carboxylate from the combined aqueous mixture into an organic phase.

35 Claims, 3 Drawing Sheets

METHODS FOR INCREASING HYDROFORMYLATION CATALYST PREFORMING RATES

This application is a National Phase Application claiming priority to PCT Application Serial No. PCT/EP2020/086386 filed Dec. 16, 2020, which claims priority to and the benefit of U.S. Provisional Application No. 62/965,464, filed Jan. 24, 2020, the disclosures of which are incorporated herein by reference in their entireties.

FIELD

The present disclosure relates generally to hydroformylation.

BACKGROUND

Hydroformylation, also referred to as the oxo process, represents the conversion of an olefin into an aldehyde through metal-catalyzed carbonyl addition. Hydroformylation reactions may take place by contacting synthesis gas ("syngas"), a mixture of carbon monoxide (CO) and hydrogen ($H_2$), with an olefin in the presence of a suitable catalyst to form a hydroformylation reaction product. Frequently, the aldehydes within the hydroformylation reaction product are converted into alcohols through subsequent reduction, thereby forming primary alcohols having one carbon atom more than the olefin from which they were produced. Long-chain primary alcohols formed through hydroformylation and subsequent reduction may find many uses including, for example, organic solvents, detergents, surfactants, or the alcohol component of ester-based plasticizers for polymers (e.g., PVC).

Typical hydroformylation catalysts comprise a Group 9 transition metal, such as cobalt or rhodium. Hydridocobalt tetracarbonyl ($HCo(CO)_4$) is a particularly efficacious Group 9 transition metal hydroformylation catalyst. In conventional hydroformylation processes, the hydroformylation catalyst may be removed (recovered) from a hydroformylation reaction product or a reduced variant thereof, and undergo subsequent recycling for promoting further use. Catalyst removal from a hydroformylation reaction product may be achieved by converting the catalyst metal, such as cobalt, into an aqueous-soluble form under oxidizing conditions so it may be separated from the organic components of the hydroformylation reaction product. The aqueous-soluble form of the catalyst metal is not catalytically active and, therefore, must be converted back into a catalytically active form before it may promote further hydroformylation. Conversion into the catalytically active form may occur in situ under hydroformylation reaction conditions, such as described in U.S. Pat. No. 4,225,458, wherein cobalt carboxylates (cobalt soaps) may be converted back into an active hydroformylation catalyst under hydroformylation reaction conditions. Other representative references describing hydroformylation reactions and various processes conducted therein include, for example, U.S. Pat. Nos. 3,234, 146 and 2,802,846.

Regenerating an active hydroformylation catalyst from a deactivated catalyst solution, referred to as "preforming" herein, is not a trivial aspect of a hydroformylation process and sometimes may occur at a rate that is much slower than desired. Identifying sources of hydroformylation catalyst preforming delays and mitigating effects thereof would be beneficial to various industries.

SUMMARY

In various embodiments, methods of the present disclosure comprise: contacting an olefinic feed with syngas and a hydroformylation catalyst comprising a Group 9 transition metal under conditions effective to form a hydroformylation reaction product; treating the hydroformylation reaction product with an aqueous carboxylic acid under oxidizing conditions to form a deactivated catalyst aqueous solution having a pH of about 4 or less; reducing the hydroformylation reaction product to form a reduced reaction product; conveying a gas stream through the reduced reaction product at a rate sufficient to strip at least some carbon dioxide therefrom, thereby forming a stripped reduced reaction product; contacting fresh caustic aqueous solution with the stripped reduced reaction product; recovering a partially spent caustic aqueous solution after contacting the stripped reduced reaction product with the fresh caustic aqueous solution; combining at least a portion of the partially spent caustic aqueous solution and the deactivated catalyst aqueous solution to form a combined aqueous mixture having a pH sufficiently acidic to decompose carbonate; extracting a Group 9 transition metal carboxylate from the combined aqueous mixture into an organic phase; and exposing the organic phase to the conditions effective to form the hydroformylation reaction product.

In other various aspects, methods of the present disclosure comprise: contacting an olefinic feed with syngas and a hydroformylation catalyst comprising a Group 9 transition metal under conditions effective to form a hydroformylation reaction product; treating the hydroformylation reaction product with an aqueous carboxylic acid under oxidizing conditions to form a deactivated catalyst aqueous solution having a pH of about 4 or less; combining a partially spent caustic aqueous solution with the deactivated catalyst aqueous solution to form a combined aqueous mixture having a pH sufficiently acidic to decompose carbonate; combining fresh caustic aqueous solution with the combined aqueous mixture after combining the partially spent caustic aqueous solution therewith, the pH of the combined aqueous mixture being at least about 7.5 after combining the fresh caustic aqueous solution; extracting a Group 9 transition metal carboxylate from the combined aqueous mixture into an organic phase; and providing the organic phase to the conditions effective to form the hydroformylation reaction product.

In still other various aspects, methods of the present disclosure comprise: forming a reduced reaction product through reduction of a hydroformylation reaction product; conveying a gas stream through the reduced reaction product at a rate sufficient to remove at least some carbon dioxide therefrom, thereby forming a stripped reduced reaction product; contacting the stripped reduced reaction product with fresh caustic aqueous solution to form a partially spent caustic aqueous solution; contacting the partially spent caustic aqueous solution with a deactivated catalyst aqueous solution to form a combined aqueous mixture having a pH sufficiently acidic to decompose carbonate, the deactivated catalyst aqueous solution comprising a Group 9 transition metal, having a pH of about 4 or less, and being obtained from a hydroformylation reaction; combining fresh caustic aqueous solution with the combined aqueous mixture after combining the partially spent caustic aqueous solution therewith, the pH of the combined aqueous mixture being at least about 7.5 after combining the fresh caustic aqueous solution; extracting a Group 9 carboxylate from the combined aqueous mixture into an organic phase; and exposing the organic phase to hydroformylation reaction conditions.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and having the benefit of this disclosure.

DETAILED DESCRIPTION

Figure 1:
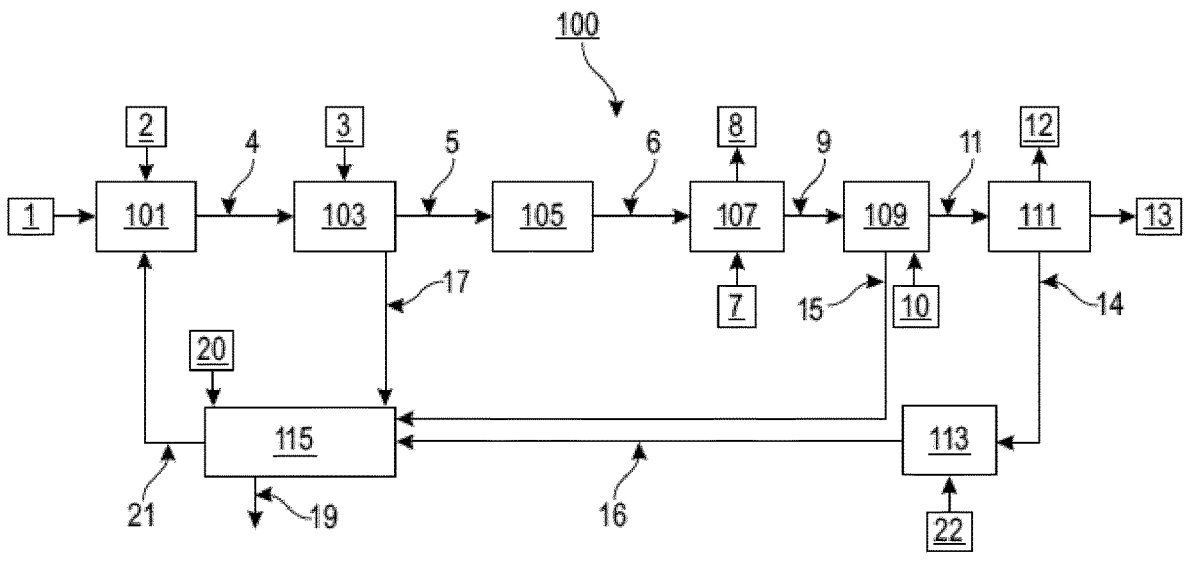
FIG. 1 is a flow diagram of a hydroformylation process implementing a first variant of the methods described herein.

The present disclosure relates to hydroformylation and, more specifically, to methods for increasing the rate of hydroformylation catalyst preforming during hydroformylation reactions.

As discussed above, catalyst preforming rates during hydroformylation are currently problematic. Surprisingly, the presence of carbonates has now been identified in the present disclosure as a source of the preforming delay. Without being bound by any theory or mechanism, it is believed that the presence of carbonates results in formation of catalyst metal carbonate compounds that must be decomposed before an active hydroformylation catalyst may be regenerated. Carbonates may be introduced to a catalyst metal undergoing recycling from several unexpected sources, as discussed herein. The present disclosure discusses how the various sources of carbonates may be addressed during hydroformylation processes to increase the rate of catalyst preforming, wherein various carbonate mitigation strategies may be implemented separately or in combination with one another depending on the level of carbonate remediation required. Advantageously, the processes for mitigating carbonates may be readily incorporated within existing hydroformylation processes, and, therefore, minimize the need for extensive process modifications.

The methods of the present disclosure are discussed further hereinafter with reference to FIG. 1, which is a diagram of a hydroformylation process in which various strategies have been implemented to mitigate the presence of carbonates when recycling catalyst metal. The methods of the present disclosure may be implemented separately or, more preferably, in combination with one other, to mitigate the presence of carbonates, particularly during catalyst preforming of a recycled hydroformylation catalyst metal, such as cobalt or another Group 9 transition metal effective for promoting hydroformylation. Mitigating the presence of carbonates may comprise removing carbon dioxide from the process stream at one or more locations, specifically by limiting the amount of carbon dioxide introduced to partially spent caustic aqueous solutions formed during hydroformylation reaction product treatment and catalyst recycling operations, thereby limiting the quantity of carbonates returned to the hydroformylation reaction with the catalyst metal, as explained in further detail herein. Additional strategies to mitigate residual carbonates within the partially spent caustic aqueous solution are also addressed herein.

Caustic aqueous solutions are known to be subject to carbon dioxide uptake from air, which may result in a concentration change of the caustic due to carbonate formation. Surprisingly, this process is not the main contributor to carbonate formation in the partially spent caustic aqueous solutions formed and employed in the disclosure herein. Instead, residual carbon dioxide from the hydroformylation reaction product or a reduced form thereof may account for a substantial majority of the carbonates formed in the partially spent caustic aqueous solution and subsequently returned to the hydroformylation reaction. The present disclosure addresses this issue in at least two complementary ways, which can be implemented separately or in combination.

Referring to FIG. 1, hydroformylation process 100 illustrates various methods to decrease the formation of catalyst metal carbonates during catalyst metal preforming. Hydroformylation 101 may be carried out by contacting olefinic feed 1 with syngas (hydrogen and carbon monoxide, e.g., a 1:1 mixture) 2 and a hydroformylation catalyst under conditions effective to form hydroformylation reaction product 4, which may comprise at least one aldehyde. Examples of suitable hydroformylation catalysts may include those comprising a Group 9 transition metal (e.g., cobalt or rhodium, preferably cobalt). Examples of suitable hydroformylation catalysts comprising cobalt include cobalt carbonyls, such as $Co_2(CO)_8$, which may convert to $HCo(CO)_4$ under high $CO/H_2$ pressures commonly encountered during hydroformylation. Suitable syngas pressures effective for forming $HCo(CO)_4$ in situ may range from about 1 MPa to about 30 MPa, with a ratio of $H_2$:CO partial pressures ranging from about 2:3 to about 3:2, preferably about 1.2:1. Suitable reaction temperatures during hydroformylation may range from about room temperature to about 200° C. (i.e., about 25° C. to about 200° C.), or any subrange in between.

Suitable olefinic feeds 1 useful in the processes described herein are not considered to be particularly limited. In some process configurations, one or more alpha olefins may comprise olefinic feed 1. Suitable alpha olefins may include, but are not limited to $C_{6+}$ alpha olefins, such as 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Internal olefins, vinylidene olefins, and the like may also comprise at least a portion of olefinic feed 1 in various process implementations. Internal olefins and/or vinylidene olefins may undergo hydroformylation in combination with alpha olefins in some process configurations. Other particularly desirable process configurations may include those in which an oligomerization reaction product of propene, butenes, and/or pentenes undergoes hydroformylation according to the disclosure herein, wherein the oligomerization reaction product may comprise a terminal or nonterminal olefinic bond.

To begin the process of catalyst recycling, the hydroformylation catalyst may be removed from hydroformylation reaction product 4 as a metal salt in metal extraction 103. In particular, hydroformylation reaction product 4 may be treated with aqueous carboxylic acid 3 under oxidizing conditions to promote oxidation and formation of a metal carboxylate, which is soluble in water. The catalyst metal may undergo oxidation in this process to produce the water-soluble form. Suitable oxidizing conditions may include, for example, air, oxygen/inert gas mixtures, oxygen/hydrocarbon gas mixtures, or the like. Mild chemical oxidants, such as hydrogen peroxide, may also be employed. Examples of suitable carboxylic acids for use in metal extraction 103 to form a water-soluble metal carboxylate include, but are not limited to, acetic acid, formic acid, and propionic acid. In the particular example of a cobalt hydroformylation catalyst, aqueous acetic acid may be used to extract cobalt into an aqueous phase in the form of cobalt acetate. The resulting deactivated catalyst aqueous solution 17 may have a pH of about 4 or less. Deactivated catalyst aqueous solution 17 may be separated from an organic phase comprising demetallized hydroformylation reaction product 5, such as via phase partitioning. Optionally, the extraction process undertaken in metal extraction 103 may be repeated until the metal content of the organic phase is decreased to a desired level. Metal extraction 103 may be carried out at a temperature and pressure to prevent the aqueous phase from boiling. For example, a temperature from about 38° C. to about 93° C., or about 65° C. to about 93° C., from about 70° C. to about 90° C., or from about 75° C. to about 85° C. may be used at a pressure of about 40 psi (276 kpa) to about 150 psi (1030 kpa). Atmospheric pressure metal extraction 103 is also contemplated in the present disclosure. Aqueous carboxylic acid 3 may be combined with hydroformylation reaction product 4 at molar excess over the stoichiometric requirement, such as about 50% to about 100% excess on a molar basis. Further processing of deactivated catalyst aqueous solution 17 and the organic phase comprising demetallized hydroformylation reaction product 5 may then take place, as described hereinafter.

The organic phase comprising demetallized hydroformylation reaction product 5 may then be reduced 105 to form reduced reaction product 6 comprising at least one alcohol. Optionally, prior to reducing, demetallized hydroformylation reaction product 5 may be distilled to remove any unreacted olefins or any unwanted side products. Alternatively or additionally, demetallized hydroformylation reaction product 5 may be subjected to hydrolysis reaction conditions to convert esters and/or acetals into alcohols and/or aldehydes. Reduction may be carried out by any technique known to one of ordinary skill in the art, such as, but not limited to, hydrogenation in the presence of hydrogen and a suitable hydrogenation catalyst (e.g., nickel, platinum, palladium, sulfided molybdenum, sulfided nickel molybdenum, sulfided cobalt molybdenum, copper chromite, and the like). One of ordinary skill in the art will be familiar with the conditions suitable for conducting a hydrogenation reaction in the presence of a particular hydrogenation catalyst.

Hydroformylation process 100 recirculates various process elements in an integrated process of hydroformylation, catalyst metal recycling and product purification as described in further detail hereinafter. The integrated process may be conducted such that limited carbonates are returned to hydroformylation 101. In one particular aspect, it has been found that carbon dioxide may be present in reduced reaction product 6, which may undesirably affect (lower) the rate of catalyst preforming when transported back to deactivated catalyst aqueous solution 17 in the form of dissolved carbonates. In particular, carbon dioxide may be carried forward in the integrated process in the form of dissolved carbonates from reduced reaction product 6 to hydroformylation 101 via a partially spent caustic aqueous solution in which carbonates have formed in a reaction between caustic (e.g., NaOH) and the carbon dioxide, as explained further herein. Once the carbonates contact deactivated catalyst aqueous solution 17, undesired preforming delays may occur due to catalyst metal carbonate formation (e.g., cobalt carbonate) upon returning the catalyst metal to hydroformylation 101. Accordingly, the present disclosure takes various measures to mitigate the presence of carbon dioxide in reduced reaction product 6 and to promote removal of carbonates in other steps of hydroformylation process 100 so that minimal catalyst metal carbonate is returned to hydroformylation 101.

Referring still to FIG. 1, reduced reaction product 6 may be subjected to gas stripping 107 following reduction to remove at least some of the carbon dioxide therefrom. Gas stripping 107 may employ stripping gas 7 to promote physical desorption of carbon dioxide from reduced reaction product 6 prior to its further processing. In particular, reduced reaction product 6 may be purged with stripping gas 7 during gas stripping 107 to form stripped reduced reaction product 9. Stripping gas 7 may be any gas that will effectively remove (strip/desorb) at least some carbon dioxide from reduced reaction product 7 and carry the carbon dioxide into effluent 8. Examples of suitable stripping gasses include, but are not limited to, an inert gas (e.g., nitrogen, helium, or argon or natural gas). Stripping gas 7 may be conveyed through reduced reaction product 6 at a rate effective to remove at least a portion of the carbon dioxide therefrom, for example, from about 300 pounds/hour (about 136 kg/hour) to about 650 pounds/hour (about 295 kg/hour), or from about 375 pounds/hour (about 170 kg/hour) to about 500 pounds/hour (about 227 kg/hour), or from about 425 pounds/hour (about 193 kg/hour) to about 475 pounds/hour (about 215 kg/hour). Higher gas flow rates of stripping gas 7 may promote removal of higher quantities of carbon dioxide from reduced reaction product 6. Although not shown, stripping gas 7 may be recirculated to gas stripping 107, if desired. Gas stripping 107 may be conducted in any suitable location, such as a tower or vessel fed with reduced reaction product 6.

After gas stripping 107 has taken place, stripped reduced reaction product 9 may then be contacted with caustic aqueous solution 10 in caustic treatment 109 to afford an organic phase comprising partially purified alcohols 11 and an aqueous phase comprising a partially spent caustic aqueous solution 15. Caustic aqueous solution 10 may be fresh caustic that contains limited carbonates and has not previously been used for promoting product purification. The aqueous and organic phases may be separated from one another by phase partitioning for further processing. As used herein, the term "caustic" refers to a basic alkali metal or alkaline earth metal salt, such as a hydroxide including, but not limited to, sodium hydroxide, lithium hydroxide, potassium hydroxide, magnesium hydroxide, or the like. The term "partially spent" means that the concentration or amount of caustic in the aqueous solution has been decreased in the course of contacting stripped reduced reaction product 9, but at least some alkalinity remains. Preferably the partially spent caustic aqueous solution has a pH higher than 7. One of ordinary skill in the art will be familiar with reasons for contacting stripped reduced reaction product 9 with caustic aqueous solution 10, such as to remove acidic impurities arising from hydroformylation 101, the reaction taking place in reduction 105, or during metal extraction 103. One having ordinary skill in the art will also be familiar with suitable conditions and equipment for contacting stripped reduced reaction product 9 with caustic aqueous solution 10 to remove acid impurities, such as inline mixers, settling tanks, batch reactors, and the like. Such conditions and equipment may be substantially identical to contacting conditions used for removing acidic impurities when gas stripping 107 is not performed, as in conventional hydroformylation processes.

It is to be understood that gas stripping 107 is not necessary for performing further procedures described herein for mitigating the presence of carbonates, but gas stripping 107 may be highly beneficial for process efficiency. If gas stripping 107 is not performed, the carbonate content of partially spent caustic aqueous solution 15 may be very high, which correspondingly results in greater carbon dioxide release during subsequent processing operations described hereinafter. Excessive carbon dioxide release of this type may cause unwanted foaming and process upsets. As such, it can be highly beneficial to remove as much carbon dioxide as possible by performing gas stripping 107.

The aqueous phase comprising partially spent caustic aqueous solution 15 may retain sufficient alkalinity to perform other process operations, as described hereinafter. Advantageously, reuse of partially spent caustic aqueous solution 15 may decrease the need to supply fresh caustic aqueous solution to hydroformylation process 100, thereby simplifying process logistics and decreasing supply costs. Even with removal of a portion of the carbon dioxide from reduced reaction product 6, some carbon dioxide may still remain and undergo conversion to carbonates during caustic treatment 109. Residual carbonates formed in partially spent caustic aqueous solution 15 may result in delayed catalyst preforming when used in supporting other process operations, particularly when converting the catalyst metal into a suitable form for recycling as discussed further below. Thus, a second aspect of the present disclosure addresses mitigation of the carbonates in partially spent caustic aqueous solution 15, as discussed further herein. Like gas stripping 107, the further process operations for mitigating carbonates in partially spent caustic aqueous solution 15 may be performed in conjunction with gas stripping 107, or the additional carbonate mitigation of partially spent caustic aqueous solution 15 may be omitted if the residual carbonate levels therein are sufficiently low following gas stripping 107. Preferably, both gas stripping 107 and additional carbonate removal from partially spent caustic aqueous solution 15 are performed.

The carbonate content of partially spent caustic aqueous solution 15 may be decreased significantly by performing gas stripping 107 upon reduced reaction product 6. By performing gas stripping 107, carbon dioxide concentrations within stripped reduced reaction product 9 may decreased to such an extent that partially spent caustic aqueous solution 15 contains not more than about 0.16 mol carbonate/kg partially spent aqueous caustic, or not more than about 0.10 mol carbonate/kg, or not more than about 0.5 mol carbonate/kg, or not more than 0.05 mol carbonate/kg. By performing gas stripping 107, carbonate concentrations in partially spent caustic aqueous solution 15 may advantageously range from 0 mol/kg to about 0.16 mol/kg, from about 0.01 mol/kg to about 0.1 mol/kg, or from about 0.02 mol/kg to about 0.5 mol/kg.

While gas stripping 107 may significantly decrease the carbonate content of partially spent caustic aqueous solution 15, additional reduction of the carbonate content may still be desirable to support a specified rate of catalyst preforming. As described hereinbelow, partially spent caustic aqueous solution 15 may be acidified during further use to promote removal of residual carbonates via carbonic acid decomposition. Advantageously, such processes integrate well with the acidic nature of deactivated catalyst aqueous solution 17. Before describing such further operations for removing carbonates from partially spent caustic aqueous solution 15 in further detail, additional process operations employed in conjunction with recycling of the catalyst metal and catalyst preforming will first be described.

Referring still to FIG. 1, organic phase 11 may be distilled 111, which may separate light organic fraction 12, alcohols 13, and heavy organic fraction 14 (e.g., $C_9$ to $C_{18}$ carboxylic acids and carboxylate esters) from one another. Heavy organic fraction 14 is also referred herein as "non-distilled bottoms organic fraction". Heavy organic fraction 14 may be obtained as a bottoms fraction that is then provided as a precursor to an organic phase used for extracting the catalyst metal from deactivated catalyst aqueous solution 17. Specifically, heavy organic fraction 14 may be combined with fresh caustic aqueous solution 22 to form organic soaps 16 (e.g., alkali or alkaline earth metal carboxylates) in soap formation 113. Organic soaps 16 may comprise about 90% organic materials by weight, with about 10% by weight of the organic materials being dissolved. Some organic soap formation may also have previously occurred in caustic treatment 109, with those organic soaps being fed forward with partially spent caustic aqueous solution 15, as described further below. The organic soaps formed in partially spent caustic aqueous solution 15 may arise primarily from a reaction of caustic with a carboxylic acid impurity (i.e., via direct salt formation), whereas organic soaps 16 formed from heavy organic fraction 14 may result primarily from ester hydrolysis.

Figure 2:
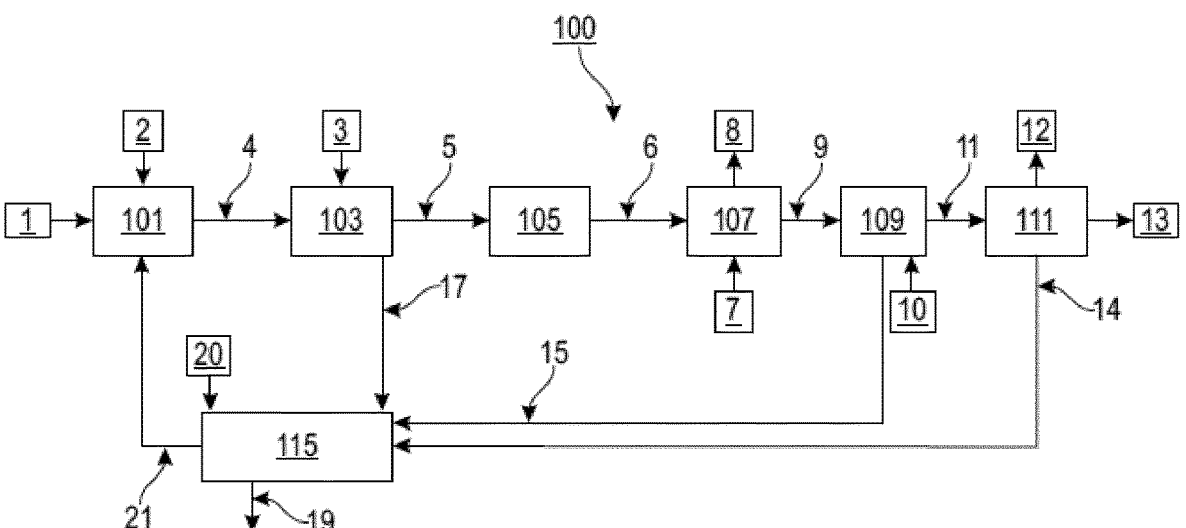
FIG. 2 is a flow diagram of a hydroformylation process implementing a second variant of the methods described herein.

Organic soaps 16 may then be combined with deactivated catalyst aqueous solution 17 at blending operation 115 to form a combined aqueous mixture comprising an organic phase and an aqueous phase to promote catalyst metal extraction. As shown in FIG. 1, organic soaps 16 are formed prior to contacting deactivated catalyst aqueous solution 17 at blending operation 115. Alternately, heavy organic fraction 14 may be provided to blending operation 115 without forming organic soaps 16 beforehand, as shown in the alternative process configuration of FIG. 2. When heavy organic fraction 14 is provided directly to blending operation 115, organic soaps 16 may be formed under a first set of reaction conditions at blending operation 115, followed by catalyst metal extraction into an organic phase comprising organic soaps 16 under a second set of reaction conditions.

Typically, the pH of deactivated catalyst aqueous solution 17 is about 4 or less (e.g., from about 1 to about 4). In order to drive the catalyst metal from the aqueous phase into an organic phase comprising organic soaps 16, the pH needs to be increased to a value of about 7.5 or greater, which is accomplished, in part, by concurrently feeding partially spent caustic aqueous solution 15 to blending operation 115. By adding partially spent caustic aqueous solution 15 to blending operation 115 to promote the pH increase, rather than fresh caustic (as performed in conventional catalyst recycling operations), the low starting pH of deactivated catalyst aqueous solution 17 may convert residual carbonates in partially spent caustic aqueous solution 15 to carbonic acid, which subsequently decomposes to water and carbon dioxide. The carbon dioxide bubbles through the liquid to the top of the reactor, facilitated by heating and stirring of the reactor contents. Once the pH reaches a value of about 6, further carbonate decomposition becomes inefficient, and a further pH increase to a value of about 7.5 or greater may be accomplished using fresh caustic aqueous solution 20 containing as low as possible amount of carbonates. Thus, process 100 requires less caustic material input than in conventional processes, while simultaneously promoting carbonate removal as a consequence of the manner in which partially spent caustic aqueous solution 15 is exposed to the catalyst metal.

Concurrently with blending operation 115, extraction of catalyst metal into organic soaps 16 may occur (e.g., within the same reactor vessel where blending operation 115 takes place). Organic phase 21 (i.e., a catalyst metal organic soap extract) and aqueous phase 19 may then be separated from one another by phase partitioning. The original water-soluble metal carboxylate of the deactivated catalyst metal may be converted to a long-chain, organic-soluble carboxylate in this process. Since a higher pH may facilitate extraction of the catalyst metal into organic phase 21, further fresh caustic aqueous solution 20 may be introduced to blending operation 115 to raise the pH to a level sufficient to promote extraction of the catalyst metal into organic phase 21 as a metal carboxylate, specifically as a metal soap (metal carboxylate) derived from the long-chain acids provided from heavy organic fraction 14. The pH needed to facilitate this process may be about 7.5 or greater, particularly in a range of about 7.5 to about 8. Thus, the present disclosure facilitates more complete exclusion of catalyst metal carbonates, such as cobalt carbonate, during catalyst metal recycling by minimizing the presence of carbonates in partially spent caustic aqueous solution 15 used in conjunction therewith, specifically by performing gas stripping 107 upon reduced reaction product 6 and/or by combining partially spent caustic aqueous solution 15 with deactivated catalyst aqueous solution 17 at a low pH sufficiently acidic to promote decomposition of carbonates.

After catalyst metal has been extracted into organic phase 21 at blending operation 115, organic phase 21 may comprise organic soaps of the catalyst metal. Aqueous phase 19 may then be sent to waste or used to supplement other process operations, as desired. Organic phase 21 may then be conveyed to hydroformylation 101 to resume the catalytic process cycle. The deactivated catalyst metal may be preformed into an active hydroformylation catalyst (e.g., $HCo(CO)_4$) under the hydroformylation reaction conditions. Optionally, organic phase 21 may be subjected to a set of preforming conditions effective to convert the deactivated catalyst metal into its catalytically active form before being contacted with an olefinic feed in the presence of syngas, wherein the preforming conditions are different from the hydroformylation conditions.

Accordingly, methods of the present disclosure may comprise: contacting an olefinic feed with syngas and a hydroformylation catalyst comprising a Group 9 transition metal under conditions effective to form a hydroformylation reaction product; treating the hydroformylation reaction product with an aqueous carboxylic acid under oxidizing conditions to form a deactivated catalyst aqueous solution having a pH of about 4 or less; reducing the hydroformylation reaction product to form a reduced reaction product; conveying a gas stream through the reduced reaction product at a rate sufficient to strip at least some carbon dioxide therefrom, thereby forming a stripped reduced reaction product; contacting fresh caustic aqueous solution with the stripped reduced reaction product; recovering a partially spent caustic aqueous solution after contacting the stripped reduced reaction product with the fresh caustic aqueous solution; combining at least a portion of the partially spent caustic aqueous solution and the deactivated catalyst aqueous solution to form a combined aqueous mixture having a pH sufficiently acidic to decompose carbonate; extracting a Group 9 transition metal carboxylate into an organic phase; and exposing the organic phase to the conditions effective to form the hydroformylation reaction product.

The combined aqueous mixture may have a pH of at least about 7.5 in various process implementations to allow extraction of the Group 9 transition metal carboxylate to take place into the organic phase. If a pH of about 7.5 is not reached in the combined aqueous mixture, fresh caustic aqueous solution may be added.

The organic phase used to perform extraction of the catalyst metal may be combined with fresh caustic aqueous solution to form organic soaps before being combined with the deactivated catalyst aqueous solution, or the fresh caustic aqueous solution and the organic phase may be provided to the deactivated catalyst aqueous solution and subsequently undergoing in situ formation of organic soaps. Concurrently with this process, partially spent caustic aqueous solution may be provided to the deactivated catalyst aqueous solution until a pH of about 6 (e.g., about 4 to about 6, or about 5 to about 6) is reached, and fresh caustic aqueous solution may then be added to increase the pH to a value of about 7.5 or greater.

The above methods for promoting catalyst preforming (i.e. increasing the preforming rate or reducing the preforming time) employ two different procedures for decreasing carbonate formation in the partially spent caustic aqueous solution used in conjunction with catalyst metal recycling. As described above, one procedure described herein comprises stripping carbon dioxide from the reduced reaction product, and a second procedure comprises combining the partially spent caustic aqueous solution with the deactivated catalyst aqueous solution at a pH of about 4 or less prior to extracting catalyst metal into the organic phase. Once a pH of about 6 is reached, fresh caustic aqueous solution may be added to reach a higher alkaline pH (e.g., about 7.5 or greater) before extraction takes place. These two procedures may be used in conjunction with each other, as described above, or one of the procedures may be omitted, if sufficient carbon dioxide removal/carbonate mitigation may be accomplished by practicing one of the procedures alone.

In one example, carbon dioxide removal may be carried out by omitting the procedure wherein the reduced reaction product undergoes gas stripping. As above, the deactivated catalyst metal may then be extracted into the organic phase upon raising the pH of the combined aqueous mixture to about 7.5 or above. The organic phase comprising a catalyst metal carboxylate may then be exposed to hydroformylation reaction conditions to reform the active hydroformylation catalyst.

More specifically, such methods may comprise: contacting an olefinic feed with syngas and a hydroformylation catalyst comprising a Group 9 transition metal under conditions effective to form a hydroformylation reaction product; treating the hydroformylation reaction product with an aqueous carboxylic acid under oxidizing conditions to form a deactivated catalyst aqueous solution having a pH of about 4 or less; combining a partially spent caustic aqueous solution with the deactivated catalyst aqueous solution to form a combined aqueous mixture having a pH sufficiently acidic to decompose carbonate; combining fresh caustic aqueous solution with the combined aqueous mixture after combining the partially spent caustic aqueous solution therewith, such that the pH of the combined aqueous mixture is at least about 7.5 after combining the fresh caustic aqueous solution; extracting a Group 9 transition metal carboxylate from the combined aqueous mixture into an organic phase; and providing the organic phase to the conditions effective to form the hydroformylation reaction product. The organic phase may be formed from a precursor comprising a heavy organic phase, specifically a heavy organic phase comprising $C_9$ to $C_{18}$ carboxylic acids and $C_9$ to $C_{18}$ carboxylate esters, which may be hydrolyzed or neutralized to form organic soaps to promote catalyst metal extraction. The organic soaps may be provided to the combined aqueous mixture before or after adjusting the pH with the partially spent caustic aqueous solution. Catalyst metal carboxylates in the organic phase may then be contacted once more with an olefinic feed and syngas under conditions effective to convert the hydroformylation catalyst to its active form and subsequently form additional hydroformylation reaction product.

Still other methods for mitigating carbonates may comprise: forming a reduced reaction product through reduction of a hydroformylation reaction product; conveying a gas stream through the reduced reaction product at a rate sufficient to remove at least some carbon dioxide therefrom, thereby forming a stripped reduced reaction product; contacting the stripped reduced reaction product with a caustic aqueous solution to form a partially spent caustic aqueous solution; contacting the partially spent caustic aqueous solution with a deactivated catalyst aqueous solution to form a combined aqueous mixture having a pH sufficiently acidic to decompose carbonate, the deactivated catalyst aqueous solution comprising a Group 9 transition metal, having a pH of about 4 or less, and being obtained from a hydroformylation reaction; extracting a Group 9 carboxylate from the combined aqueous mixture into an organic phase; and exposing the organic phase to hydroformylation reaction conditions. A heavy organic fraction, specifically a heavy organic fraction comprising one or more $C_9$ to $C_{18}$ carboxylic acids and $C_9$ to $C_{18}$ carboxylate esters, may serves as a precursor to the organic phase use to promote extraction of the catalyst metal from the combined aqueous mixture The methods described herein may be carried out at any conventional plant equipped with various process equipment such as reactors (e.g., stirred batch reactors), separators, condensers, compressors, and the like. One of ordinary skill in the art will be familiar with such equipment and be able to utilize the same for carrying out the methods disclosed herein.

Embodiments disclosed herein include:

A. Methods for mitigating carbonates by gas stripping and acidification. The methods comprise: contacting an olefinic feed with syngas and a hydroformylation catalyst comprising a Group 9 transition metal under conditions effective to form a hydroformylation reaction product; treating the hydroformylation reaction product with an aqueous carboxylic acid under oxidizing conditions to form a deactivated catalyst aqueous solution having a pH of about 4 or less; reducing the hydroformylation reaction product to form a reduced reaction product; conveying a gas stream through the reduced reaction product at a rate sufficient to strip at least some carbon dioxide therefrom, thereby forming a stripped reduced reaction product; contacting fresh caustic aqueous solution with the stripped reduced reaction product; recovering a partially spent caustic aqueous solution after contacting the stripped reduced reaction product with the fresh caustic aqueous solution; combining at least a portion of the partially spent caustic aqueous solution and the deactivated catalyst aqueous solution to form a combined aqueous mixture having a pH sufficiently acidic to decompose carbonate; extracting a Group 9 transition metal carboxylate from the combined aqueous mixture into an organic phase; and exposing the organic phase to the conditions effective to form the hydroformylation reaction product.

B. Methods for mitigating carbonates by acidification. The methods comprise: contacting an olefinic feed with syngas and a hydroformylation catalyst comprising a Group 9 transition metal under conditions effective to form a hydroformylation reaction product; treating the hydroformylation reaction product with an aqueous carboxylic acid under oxidizing conditions to form a deactivated catalyst aqueous solution having a pH of about 4 or less; combining a partially spent caustic aqueous solution with the deactivated catalyst aqueous solution to form a combined aqueous mixture having a pH sufficiently acidic to decompose carbonate; combining fresh caustic aqueous solution with the combined aqueous mixture after combining the partially spent caustic aqueous solution therewith, the pH of the combined aqueous mixture being at least about 7.5 after combining the fresh caustic aqueous solution; extracting a Group 9 transition metal carboxylate from the combined aqueous mixture into an organic phase; and providing the organic phase to the conditions effective to form the hydroformylation reaction product.

C. Methods for mitigating carbonates by gas stripping. The methods comprise: forming a reduced reaction product through reduction of a hydroformylation reaction product; conveying a gas stream through the reduced reaction product at a rate sufficient to remove at least some carbon dioxide therefrom, thereby forming a stripped reduced reaction product; contacting the stripped reduced reaction product with fresh caustic aqueous solution to form a partially spent caustic aqueous solution; contacting the partially spent caustic aqueous solution with a deactivated catalyst aqueous solution to form a combined aqueous mixture having a pH sufficiently acidic to decompose carbonate, the deactivated catalyst aqueous solution comprising a Group 9 transition metal, having a pH of about 4 or less, and being obtained from a hydroformylation reaction; combining fresh caustic aqueous solution with the combined aqueous mixture after combining the partially spent caustic aqueous solution therewith, the pH of the combined aqueous mixture being at least about 7.5 after combining the fresh caustic aqueous solution; extracting a Group 9 carboxylate from the combined aqueous mixture into an organic phase; and exposing the organic phase to hydroformylation reaction conditions.

Each of embodiments A, B, and C may have one or more of the following additional elements in any combination:

Element 1: wherein the aqueous carboxylic acid comprises acetic acid.

Element 2: wherein the Group 9 transition metal comprises cobalt.

Element 3: wherein the hydroformylation catalyst comprises $HCo(CO)_4$.

Element 4: wherein the reduced reaction product is formed through hydrogenation of the hydroformylation reaction product.

Element 5: wherein the gas stream comprises natural gas.

Element 6: wherein the gas stream is conveyed through the reduced reaction product at a rate of about 300 pounds per hour (136 kg/hour) or more.

Element 7: wherein the partially spent caustic aqueous solution comprises about 0.16 mol or less carbonate per kg of solution.

Element 8: wherein the method further comprises distilling one or more alcohols from the reduced reaction product or the stripped reduced reaction product; obtaining a non-distilled bottoms organic fraction when distilling the one or more alcohols; and providing at least a portion of the non-distilled bottoms organic fraction as organic soaps to the combined aqueous mixture as a precursor to the organic phase.

Element 9: wherein the non-distilled bottoms organic fraction (also referred herein as heavy organic fraction) comprises one or more $C_9$-$C_{18}$ carboxylic acids, $C_9$-$C_{18}$ carboxylate esters, or any combination thereof.

Element 10: wherein the method further comprises: adjusting a pH of the combined aqueous mixture to a value of at least about 7.5 with fresh caustic aqueous solution after combining the partially spent caustic aqueous solution with the deactivated catalyst aqueous solution.

Element 11: wherein the pH sufficiently acidic to decompose carbonate is about 6 or less.

Element 12: wherein the method further comprises: reducing the hydroformylation reaction product to form a reduced reaction product; and contacting the reduced reaction product or a product formed therefrom with fresh caustic aqueous solution to form the partially spent caustic aqueous solution.

Element 13: wherein the method further comprises: distilling one or more alcohols from the reduced reaction product or the product formed therefrom; obtaining a non-distilled bottoms organic fraction when distilling the one or more alcohols; and providing at least a portion of the non-distilled bottoms organic fraction to the combined aqueous mixture as a precursor to the organic phase.

Element 14: wherein the method further comprises: conveying a gas stream through the reduced reaction product at a rate sufficient to remove at least some carbon dioxide therefrom, thereby forming a stripped reduced reaction product.

Element 15: wherein the stripped reduced reaction product is contacted with fresh caustic aqueous solution to form the partially spent caustic aqueous solution.

Element 16: wherein the reduced reaction product is formed through hydrogenation of the hydroformylation reaction product.

By way of non-limiting example, illustrative combinations applicable to A include, but are not limited to, 1 and 2; 1-3; 1 and 4; 1 and 5; 1 and 8; 1, 8 and 9; 1 and 10; 1 and 11; 1, 10 and 11; 2 and 3; 2-4; 2 and 5; 2 and 8; 2, 8 and 9; 2 and 10; 2 and 11; 2, 10 and 11; 3 and 4; 3 and 5; 3 and 8; 3 and 10; 3, 10 and 11; 3 and 11; 4 and 5; 4 and 8; 4, 8 and 9; 4 and 10; 4 and 11; 4, 10 and 11; 5 and 8; 5, 8 and 9; 5 and 10; 5 and 11; 5, 10 and 11; and 10 and 11. Illustrative combinations applicable to B include, but are not limited to, 1 and 2; 1-3; 1 and 11; 1 and 12; 1 and 13; 1, 9 and 13; 1 and 14; 1 and 15; 2 and 3; 2 and 11; 2 and 12; 2 and 13; 2, 9 and 13; 2 and 14; 2 and 15; 9 and 13; 12 and 13; 9, 12 and 13; 11 and 12; 11 and 14; 11 and 15; 12 and 14; 12 and 15; and 14 and 15. Illustrative combinations applicable to C include, but are not limited to, 2 and 4; 2 and 5; 2 and 6; 2 and 8; 2 and 9; 2 and 10; 4 and 5; 4 and 6; 4 and 8; 4 and 9; 4 and 11; 5 and 6; 5 and 8; 5 and 9; 5 and 11; 6 and 8; 6 and 9; 6 and 11; 8 and 9; 8 and 11; and 9 and 11.

To facilitate a better understanding of the present disclosure, the following examples of preferred or representative embodiments are given. In no way should the following examples be read to limit, or to define, the scope of the invention.

EXAMPLES

Example 1. A feed comprising octenes made from oligomerization of Raffinate 2 butenes was loaded into a batch reactor along with a cobalt(II) hydroformylation catalyst precursor capable of forming $HCo(CO)_4$, such that the concentration of catalyst metal in the reactor was about 3000 ppm. The cobalt (II) hydroformylation catalyst precursor was prepared from a cobalt (II) naphthenate solution containing 6 wt. % Co by adding 10 wt. % water thereto. Depending on experiment, the water was pure demineralized water, or contained 5 wt. % sodium carbonate or 5 wt. % sodium acetate. The reactor was heated to about 155° C. and syngas was added to achieve an initial syngas pressure of 300 bar. The preforming time for the catalyst was taken to be that at which a sudden decline in syngas pressure occurred which coincides with the onset of conversion. At that time, the syngas pressure was restored to 300 bar, and conversion was followed over time thereafter.

Figure 3:
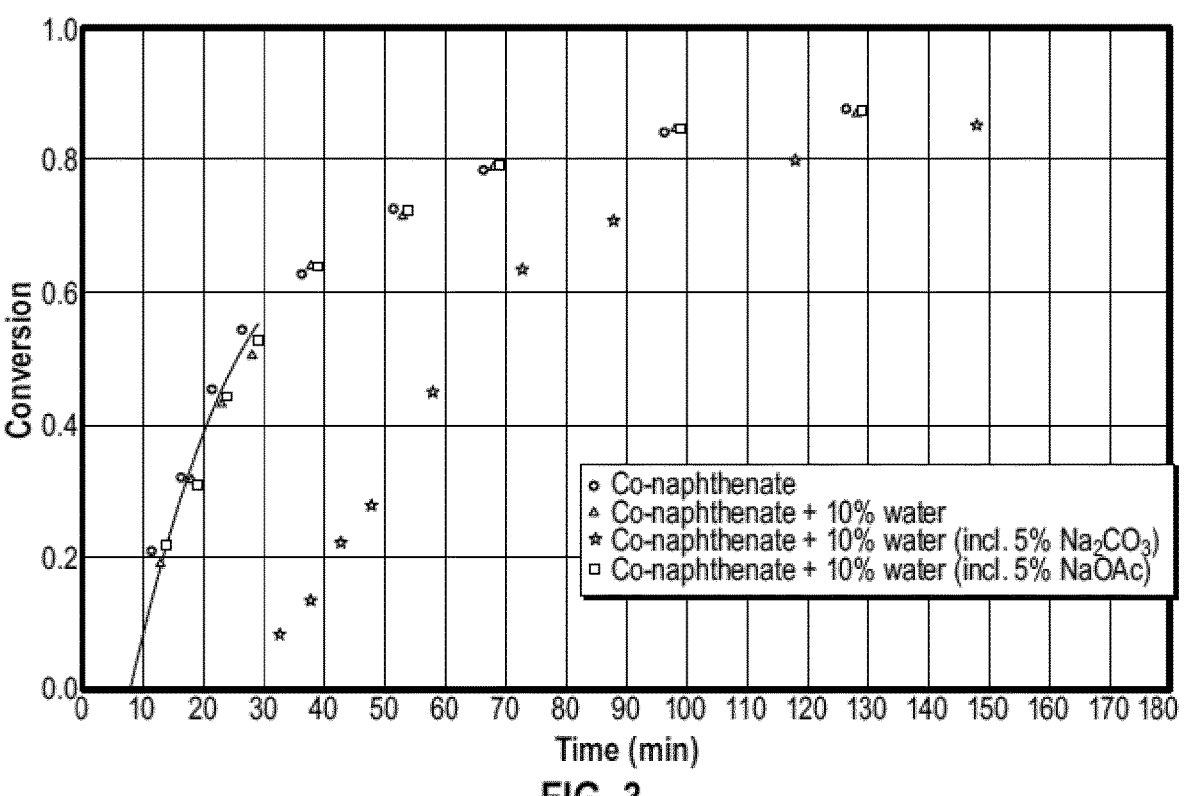
FIG. 3 is a graph showing the conversion rates of olefins to aldehydes under various conditions.

To confirm that carbonates indeed affected catalyst preforming, 5% sodium carbonate was added to the cobalt (II) naphthenate solution used in one run. The results are shown in FIG. 3, which shows a plot of the extent of conversion as a function of time. A notable delay in the onset of conversion (i.e., preforming time) was observed in the presence of the 5% sodium carbonate, as compared to the preforming time obtained in the absence of sodium carbonate. Solids also formed when the sodium carbonate was present. Other additives (see FIG. 3) did not delay the onset of catalyst preforming significantly or form a significant amount of solids.

Figure 4:
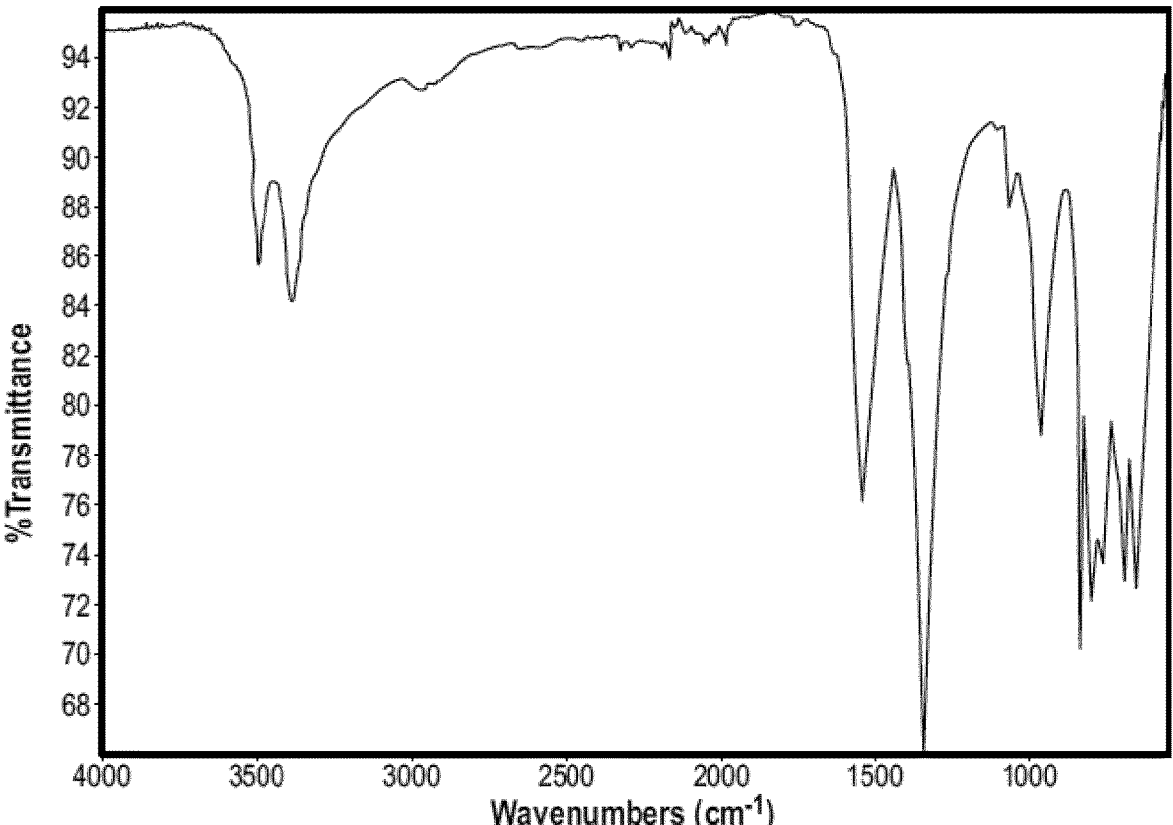
FIG. 4 is an infrared spectrum of a precipitate formed when regenerating a cobalt hydroformylation catalyst in the presence of sodium carbonate.

A solid formed in the run in which sodium carbonate was added. FIG. 4 shows an infrared spectrum of the solid obtained in the presence of sodium carbonate. Analysis of the infrared spectrum showed a good peak match for cobalt carbonate. A solid formed under plant recycling conditions exhibited an infrared spectrum very similar in appearance to the infrared spectrum shown in FIG. 4.

Figure 5:
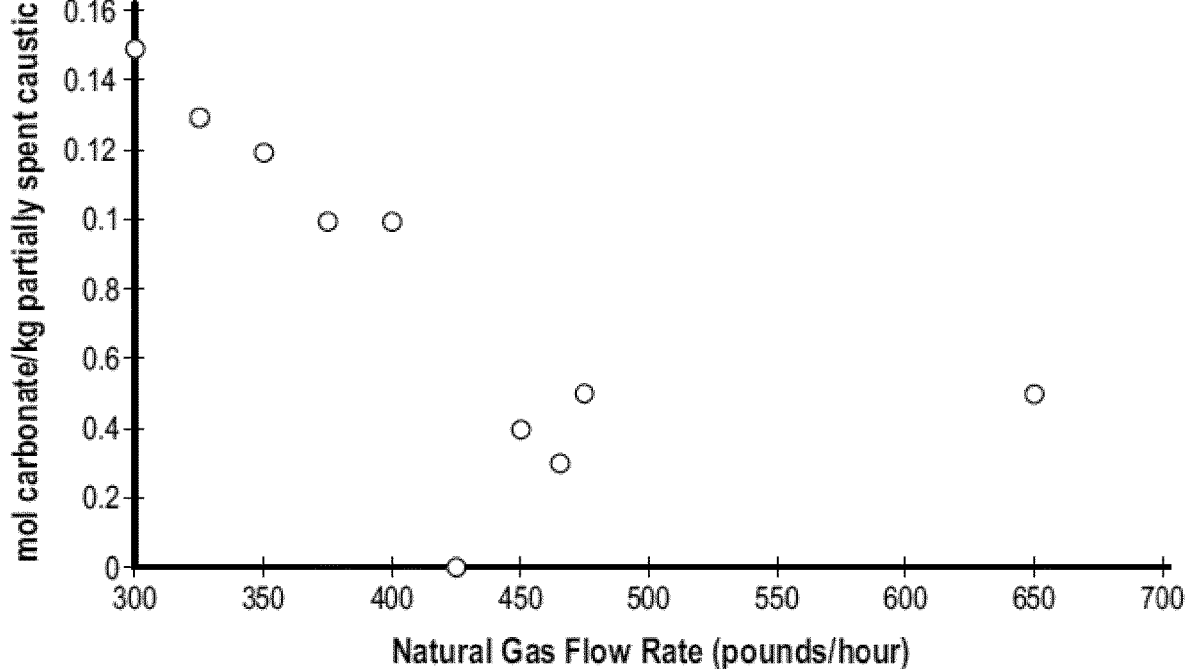
FIG. 5 is a graph showing the effect of gas stripping a reduced hydroformylation reaction product and the resulting amount of carbonate formed in a partially spent caustic aqueous solution contacted with the reduced hydroformylation reaction product.

Example 2. To illustrate the effectiveness of natural gas stripping in decreasing the quantity of carbonates in the partially spent caustic aqueous solution, natural gas was passed through a reduced hydroformylation reaction product at various rates. Caustic aqueous solution was then contacted with the stripped hydroformylation reaction product, and the carbonate concentration of the partially spent caustic aqueous solution was then determined. The carbonate concentration was determined by acidifying the partially spent caustic aqueous solution with excess sulfuric acid and measuring the volume of carbon dioxide liberated therefrom. Results are shown in Table 1 below and in FIG. 5.

TABLE 1

| Stripping Condition # | Natural Gas Stripping Rate (lb/hour) | Run | Carbonate Concentration (mol $CO_3$/kg partially spent caustic) |
|---|---|---|---|
| 1 | 300 (136 kg/hour) | a | 0.15 |
| 2 | 325 (147 kg/hour) | a | 0.13 |
| | | b | 0.02 |
| 3 | 350 (157 kg/hour) | a | 0.12 |
| | | b | 0.08 |

TABLE 1-continued

| Stripping Condition # | Natural Gas Stripping Rate (lb/hour) | Run | Carbonate Concentration (mol CO₃/kg partially spent caustic) |
|---|---|---|---|
| 4 | 375 (170 kg/hour) | a | 0.1 |
| | | b | 0.11 |
| 5 | 400 (181 kg/hour) | a | 0.1 |
| | | b | 0.07 |
| 6 | 425 (193 kg/hour) | a | 0 |
| 7 | 450 (204 kg/hour) | a | 0.04 |
| 8 | 465 (211 kg/hour | a | 0.03 |
| 9 | 475 (215 kg/hour) | a | 0.05 |
| 10 | 650 (295 kg/hour) | a | 0.05 |

Notably, a higher stripping rate resulted in a lower carbonate concentration in the partially spent caustic aqueous solution, indicating that natural gas stripping may be a viable technique for reducing the exposure of the catalyst metal to carbonate during catalyst recovery and preforming.

The disclosure herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. All numerical values within the detailed description and the claims herein are modified by "about" or "approximately" with respect to the indicated value, and take into account experimental error and variations that would be expected by a person having ordinary skill in the art. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention.

The invention claimed is:

1. A method comprising:
contacting an olefinic feed with syngas and a hydroformylation catalyst comprising a Group 9 transition metal under conditions effective to form a hydroformylation reaction product;
treating the hydroformylation reaction product with an aqueous carboxylic acid under oxidizing conditions to form a deactivated catalyst aqueous solution having a pH of about 4 or less;
reducing the hydroformylation reaction product to form a reduced reaction product;
conveying a gas stream through the reduced reaction product at a rate sufficient to strip at least some carbon dioxide therefrom, thereby forming a stripped reduced reaction product;
contacting fresh caustic aqueous solution with the stripped reduced reaction product;
recovering a partially spent caustic aqueous solution after contacting the stripped reduced reaction product with the fresh caustic aqueous solution;
combining at least a portion of the partially spent caustic aqueous solution and the deactivated catalyst aqueous solution to form a combined aqueous mixture having a pH sufficiently acidic to decompose carbonate;
extracting a Group 9 transition metal carboxylate from the combined aqueous mixture into an organic phase; and
exposing the organic phase to the conditions effective to form the hydroformylation reaction product.

2. The method of claim 1, wherein the aqueous carboxylic acid comprises acetic acid.

3. The method of claim 1, wherein the Group 9 transition metal comprises cobalt.

4. The method of claim 1, wherein the hydroformylation catalyst comprises $HCo(CO)_4$.

5. The method of claim 1, wherein the reduced reaction product is formed through hydrogenation of the hydroformylation reaction product.

6. The method of claim 1, herein the gas stream comprises natural gas.

7. The method of claim 1, wherein the gas stream is conveyed through the reduced reaction product at a rate of about 300 pounds per hour (136 kg/hour) or more.

8. The method of claim 1, wherein the partially spent caustic aqueous solution comprises about 0.16 mol or less carbonate per kg of solution.

9. The method of claim 1, further comprising:

distilling one or more alcohols from the reduced reaction product or the stripped reduced reaction product;

obtaining a non-distilled bottoms organic fraction when distilling the one or more alcohols; and providing at least a portion of the non-distilled bottoms organic fraction as organic soaps to the combined aqueous mixture as a precursor to the organic phase.

10. The method of claim 9, wherein the non-distilled bottoms organic fraction comprises one or more C9-C18 carboxylic acids, C9-C18 carboxylate esters, or any combination thereof.

11. The method of claim 1, further comprising:

adjusting a pH of the combined aqueous mixture to a value of at least about 7.5 with fresh caustic aqueous solution after combining the partially spent caustic aqueous solution with the deactivated catalyst aqueous solution.

12. The method of claim 1, wherein the pH sufficiently acidic to decompose carbonate is about 6 or less.

13. A method comprising:

contacting an olefinic feed with syngas and a hydroformylation catalyst comprising a Group 9 transition metal under conditions effective to form a hydroformylation reaction product;

treating the hydroformylation reaction product with an aqueous carboxylic acid under oxidizing conditions to form a deactivated catalyst aqueous solution having a pH of about 4 or less;

combining a partially spent caustic aqueous solution with the deactivated catalyst aqueous solution to form a combined aqueous mixture having a pH sufficiently acidic to decompose carbonate;

combining fresh caustic aqueous solution with the combined aqueous mixture after combining the partially spent caustic aqueous solution therewith, the pH of the combined aqueous mixture being at least about 7.5 after combining the fresh caustic aqueous solution;

extracting a Group 9 transition metal carboxylate from the combined aqueous mixture into an organic phase; and providing the organic phase to the conditions effective to form the hydroformylation reaction product.

14. The method of claim 13, wherein the carboxylic acid comprises aqueous acetic acid.

15. The method of claim 13, wherein the Group 9 transition metal comprises cobalt.

16. The method of claim 13, wherein the hydroformylation catalyst comprises $HCo(CO)_4$.

17. The method of claim 13, further comprising:

reducing the hydroformylation reaction product to form a reduced reaction product; and contacting the reduced reaction product or a product formed therewith with fresh caustic aqueous solution to form the partially spent caustic aqueous solution.

18. The method of claim 17, further comprising:

distilling one or more alcohols from the reduced reaction product or the product formed therewith;

obtaining a non-distilled bottoms organic fraction when distilling the one or more alcohols; and providing at least a portion of the non-distilled bottoms organic fraction to the combined aqueous mixture as a precursor to the organic phase.

19. The method of claim 18, wherein the non-distilled bottoms organic fraction comprises one or more C9-C18 carboxylic acids, C9-C18 carboxylate esters, or any combination thereof.

20. The method of claim 13, further comprising:

conveying a gas stream through the reduced reaction product at a rate sufficient to remove at least some carbon dioxide therefrom, thereby forming a stripped reduced reaction product.

21. The method of claim 20, wherein the gas stream comprises natural gas.

22. The method of claim 20, wherein the stripped reduced reaction product is contacted with fresh caustic aqueous solution to form the partially spent caustic aqueous solution.

23. The method of claim 17, wherein the reduced reaction product is formed through hydrogenation of the hydroformylation reaction product.

24. The method of claim 20, wherein the gas stream is conveyed through the reduced reaction product at a rate of about 300 pounds per hour (136 kg/hour) or more.

25. The method of claim 20, wherein the partially spent caustic aqueous solution comprises about 0.16 mol or less carbonate per kg of solution.

26. The method of claim 13, wherein the pH sufficiently acidic to decompose carbonate is about 6 or less.

27. A method comprising:

forming a reduced reaction product through reduction of a hydroformylation reaction product;

conveying a gas stream through the reduced reaction product at a rate sufficient to remove at least some carbon dioxide therefrom, thereby forming a stripped reduced reaction product;

contacting the stripped reduced reaction product with fresh caustic aqueous solution to form a partially spent caustic aqueous solution;

contacting the partially spent caustic aqueous solution with a deactivated catalyst aqueous solution to form a combined aqueous mixture having a pH sufficiently acidic to decompose carbonate, the deactivated catalyst aqueous solution comprising a Group 9 transition metal, having a pH of about 4 or less, and being obtained from a hydroformylation reaction;

combining fresh caustic aqueous solution with the combined aqueous mixture after combining the partially spent caustic aqueous solution therewith, the pH of the combined aqueous mixture being at least about 7.5 after combining the fresh caustic aqueous solution;

extracting a Group 9 carboxylate from the combined aqueous mixture into an organic phase; and exposing the organic phase to hydroformylation reaction conditions.

28. The method of claim 27, wherein the gas stream comprises natural gas.

29. The method of claim 27, wherein the Group 9 transition metal comprises cobalt.

30. The method of claim 27, wherein the reduced reaction product is formed through hydrogenation of the hydroformylation reaction product.

31. The method of claim 27, wherein the gas stream is conveyed through the reduced reaction product at a rate of about 300 pounds per hour (136 kg/hour) or more.

32. The method of claim 27, wherein the partially spent caustic aqueous solution comprises about 0.16 mol or less carbonate per kg of solution.

33. The method of claim 27, further comprising:

distilling one or more alcohols from the reduced reaction product or the stripped reduced reaction product;

obtaining a non-distilled bottoms organic fraction when distilling the one or more alcohols; and providing at least a portion of the non-distilled bottoms organic fraction to the combined aqueous mixture as a precursor to the organic phase.

34. The method of claim 33, wherein the non-distilled bottoms organic fraction comprises one or more C9-C18 carboxylic acids, C9-C18 carboxylate esters, or any combination thereof.

35. The method of claim 27, wherein the pH sufficiently acidic to decompose carbonate is about 6 or less.

* * * * *